(12) United States Patent
Oshida

(10) Patent No.: US 6,575,744 B1
(45) Date of Patent: Jun. 10, 2003

(54) MIRROR

(76) Inventor: Yoshiki Oshida, 310 Haddonfield Dr., DeWitt, NY (US) 13214

(*) Notice: Subject to any disclaimer, the term of this patent is extended or adjusted under 35 U.S.C. 154(b) by 0 days.

(21) Appl. No.: 10/086,364

(22) Filed: Mar. 4, 2002

(51) Int. Cl.$^7$ ............................................... A61C 1/00
(52) U.S. Cl. ........................ 433/31; 359/872; 362/138
(58) Field of Search ..................... 433/30, 31; 362/138, 362/139; 359/872, 875, 876, 877

(56) References Cited

U.S. PATENT DOCUMENTS

| | | | |
|---|---|---|---|
| 2,948,912 A | * 8/1960 | Wisdom | |
| 4,261,637 A | * 4/1981 | King | 433/30 |
| 4,408,991 A | * 10/1983 | Engel | 433/30 |
| 5,139,421 A | * 8/1992 | Verderber | 433/31 |
| 5,654,824 A | * 8/1997 | Tarr et al. | 359/872 |
| 5,655,904 A | 8/1997 | Usui et al. | |
| 5,741,132 A | 4/1998 | Usui et al. | |
| 5,959,792 A | * 9/1999 | Ibrahim | 359/872 |
| 2002/0171955 A1 | * 11/2002 | Berger | 359/875 |

* cited by examiner

*Primary Examiner*—Todd E. Manahan
(74) *Attorney, Agent, or Firm*—Breiner & Breiner, L.L.C.

(57) ABSTRACT

A mirror for examining a confined area such as an intraoral cavity including posterior teeth, distal and/or lingual sides of teeth, is provided. The mirror includes a lit fog-free and contaminant-free mirror. Basically, the mirror includes a holding stem component and a mirror component. In the holding stem portion, a battery, motor, and on/off switch and rotation speed controlling device are present. In the mirror portion, a mirror is adhered to a rotatable disk, which rotates inside a circular concave housing and is driven by a shaft which is connected to a shaft in the holding stem component via a connecting mechanism. The circular concave housing has an outer circular surrounding collar which includes a plurality of sub-collars of irregular shapes. When the mirror on the rotatable disk is rotating, air turbulence is generated to spin off any dust, debris, contaminant, and moisture from the mirror surface. The mirror also includes an illuminating light to which electric power is supplied from an installed battery. Hence, the mirror surface is bright enough even when posterior teeth, distal and lingual sides of the teeth are observed and is moisture-free and dust-free.

8 Claims, 2 Drawing Sheets

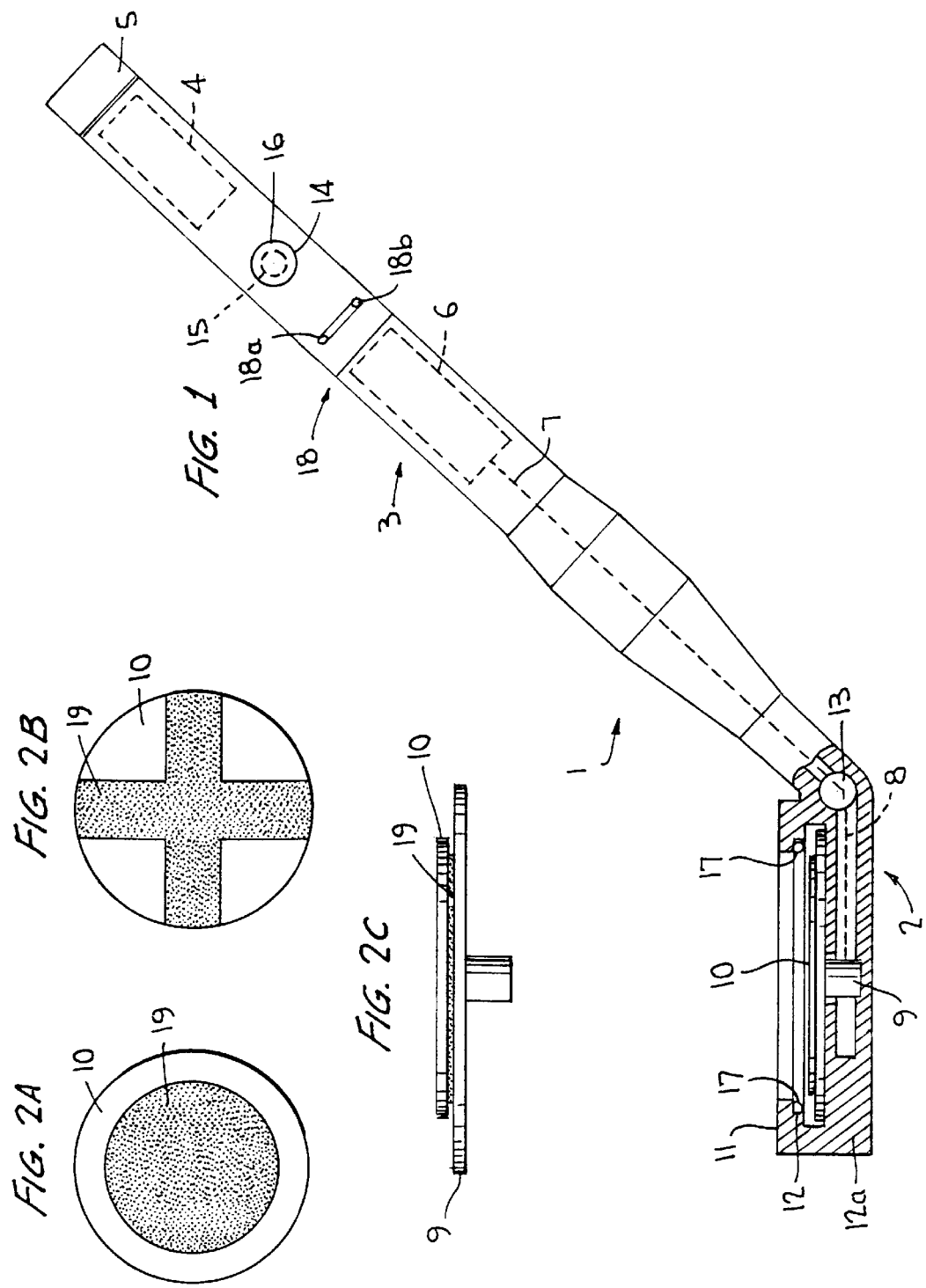

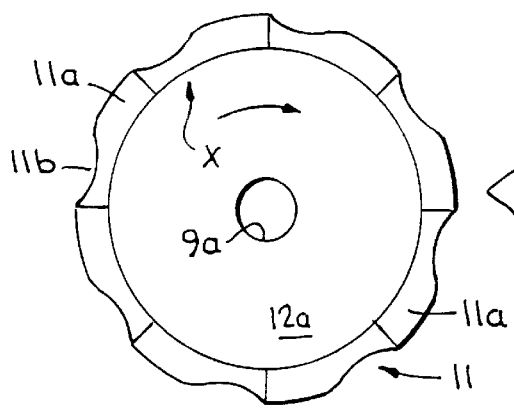
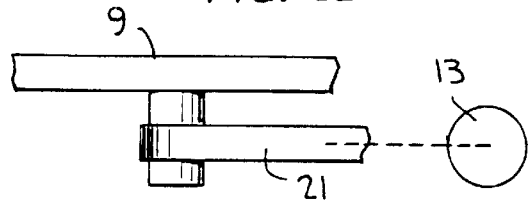
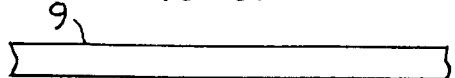
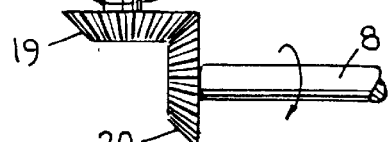
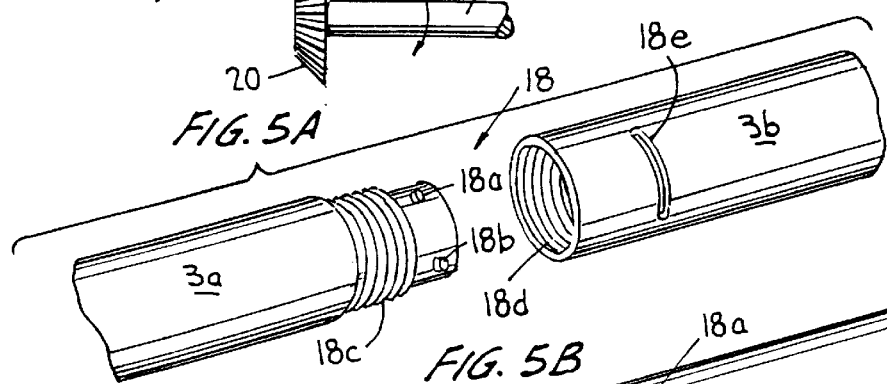
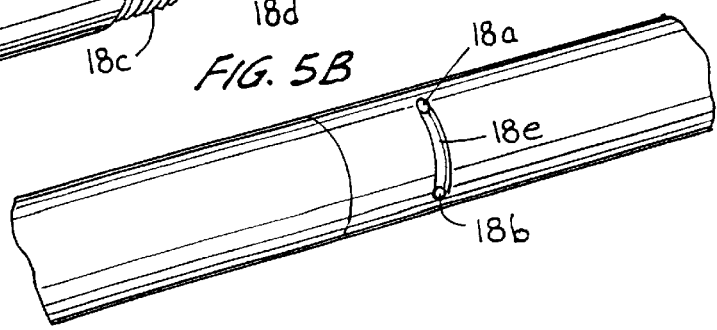

MIRROR

FIELD OF INVENTION

The present invention relates to a mirror which can be effectively used when a small or occluded area is examined. Specifically, the present invention directly relates to a dental mirror which is used for diagnosing, treating or observing an intraoral healthy or diseased portion of a patient.

BACKGROUND OF THE INVENTION

When a small area, specifically the intraoral cavity, is examined in order to diagnose, treat, or observe a diseased portion, there are several portions of the teeth which are very hard to be treated/observed without a mirror. These areas include posterior teeth in general, the distal sides of the teeth, and the lingual sides of the teeth. Conventionally, a lighting device is provided at the upper front area of a dental chair and the externally illuminating light is directed into an intraoral cavity of a patient. A dental professional (such as a dentist, dental hygienist, or dental assistant) will then manipulate a conventional type of a dental mirror to reflect the externally illuminating light to a portion of the tooth which is about to be examined so that the diseased portion can be reflected and displayed on a conventional type of dental mirror. The aforementioned type of dental mirror is made of either a metal or plastic holding stem. The reflecting mirror portion (which is made of either a plastic coated mirror or glass coated mirror) and the holding stem are formed as a unified structure. Prior to a diagnosing use with each patient, the unified structure of the dental mirror is conventionally sterilized either by an autoclave heating area high temperature and high pressure or immersing the dental mirror in an antiseptic liquid. Due to the current situation, such as intrahospital infection and/or AIDS, the whole structure of the dental mirror can be made of plastic and used as a disposable dental mirror.

Using the aforementioned dental mirror, the dentist must display a diseased portion of the teeth of a patient on a mirror portion by aid of the externally reflected light which must be illuminated on the mirror surface while the dentist manipulates the mirror at an incident angle and distance from the externally illuminating light source/device. Accordingly, providing an appropriate setting of the externally illuminating light device and reflecting surface of the dental mirror is mandatory for performing an accurate dental diagnosis and/or treatment.

As a result, a dentist requires skill to manipulate the dental mirror. There could exist a portion, in particularly the posterior teeth in general, and the distal and lingual sides of teeth, where the reflecting light cannot reach. In some cases, a dentist's head might block the illuminating light into the intraoral cavity of a patient since the illuminating light is coming from above his head. On such an occasion, the reflecting angle of the external light is subjected to fine adjustment in order to maintain clear examination of the diseased portion. When fine adjusting the incident angle of the external lighting device, however, the illuminating light will irradiate a patient's face. Hence, in many cases, not only a dentist but also a patient might be blinded by the reflecting light or discomforted by the brightness of the light and heat generated by the reflecting light.

Additionally, the conventional type of dental mirror becomes foggy due mainly to high humidity and temperature of the inhaled air during respiration activity of a patient when the mirror is inserted into the patient's mouth. Accordingly, once the surface of the dental mirror becomes foggy, it becomes very difficult to diagnose or treat appropriately and observe clearly the diseased portion of the teeth in a foggy mirror. When the dental mirror gets foggy, the dentist removes the mirror from the patient's mouth, wipes and dries the moisture before reinserting the mirror into the patient's mouth.

As discussed above, the fine adjustment of the reflecting light to shine the light on the diseased portion of the teeth and cleaning/drying of the foggy surface of dental mirrors are inconvenient for dentists. Hence the development of a fogless mirror with a built-in illumination system has been needed.

U.S. Pat. No. 5,655,904 issued on Aug. 12, 1997 to M. Usui and Y. Oshida discloses a dental mirror which is characterized by the rear side of the mirror being situated inside a concave-shaped canister filled with substances which can generate appropriate heat to prevent a foggy condition on the front surface of the dental mirror when the mirror is exposed to a high humid intraoral environment. Another patent, U.S. Pat. No. 5,741,132 issued on Apr. 21, 1998 to M. Usui, Y. Oshida, and S. Hata, discloses a mirror for dental examination which is characterized by the rear side of the mirror being kept inside a concave-shaped hollow structure in which an illuminating light source and heating source are installed, so that the front surface of the mirror can be lit and will not become foggy.

However, there are additional problems to be solved with a dental mirror. When a tooth structure is treated using a dental drill to prepare a restoration treatment, chips and debris of a tooth structure will cover the dental mirror. This dust further obstructs clear observation and proper treatment. Again when the surface of the dental mirror is covered with these particles, a dentist has to remove the mirror from the patients mouth, clean it and reinsert it. This additional task is inconvenient for both a patient and a dentist and causes chair-side time with unnecessarily proloned and unconscious fatigue. However, these problems are not solved by the prior art, such as the aforementioned U.S. Pat. Nos. 5,655,904 and 5,741,132.

SUMMARY OF THE INVENTION

In view of the foregoing, it is an object of the present invention to provide a mirror for examining a small area (specifically, an intraoral cavity) which prevents a foggy surface when the mirror is used in a high humid intraoral environment and a particle-free surface when a tooth structure is mechanically treated, and includes a built-in reflecting light device to illuminate the diseased portion of the intraoral cavity so that both patient and dentist will not be blinded by light and will not feel discomfort due to the heat generated by the external light and dental performance (including diagnosing, treating, and observing the diseased tooth structure). Accordingly, the present invention provides a fog-free and particle-free mirror with a built-in light for examining a small area, including an intraoral cavity.

In order to achieve the aforementioned object of the present invention, an examination unit which is to be inserted in an intraoral cavity to examine a diseased portion is provided at the distal end portion of a holding stem member which is held by a dentist while the dentist is operating the mirror alone or treating a tooth using a dental device by the other hand simultaneously. The mirror of the invention for a dental examination is used for diagnosing and treating the diseased portion of the mouth (particularly teeth) by an aid of the examination unit and is further characterized by comprising (1) a built-in light illuminating means to supply an illuminating light onto a diseased portion so that the diseased portion can be observed on the mirror by virtue of light being reflected on mirror surface, (2) a mirror portion which is rotated by a built-in battery-driven motor, and (3) a holding stem portion in which a battery, motor connecting mechanics, an on/off switch, and a rotating speed controlling mechanism are built in.

The present mirror for dental examination is moreover characterized by the lighting means which can be a micro-bulb, optical fiber, light emission diode (LED) or the like.

Furthermore, the mirror of the invention for dental examinations is characterized by a battery supply, or other power source, as an electric power source to the lighting means and a motor which indirectly rotates the dental mirror. The battery can be an replaceable dry battery or a rechargeable battery.

BRIEF DESCRIPTION OF THE DRAWINGS

The above and many other objects, features and advantages of the present invention will be more fully understood from the ensuing detailed description of the preferred embodiments of the present invention. That being stated, the following description should be read in conjunction with the accompanying drawings wherein FIG. 1 shows a general view of the structure of the present invention with a partial cross-section of the mirror component;

FIGS. 2A–2C show the mirror surface and examples of how to apply the adhering agent or tape onto a rear surface of the mirror, 2A being in a circular manner, and 2B being cross-shaped;

FIGS. 3A and 3B show examples of shapes for the circular concave portion that is defined by surrounding collars 11 comprising a plurality of sub-collars 11a;

FIGS. 4A and 4B show examples of a connecting method between the shaft 8 and rotatable disk 9, FIG. 2A using two bevel gears, and FIG. B a belt; and FIGS. 5A and 5B show a method of assembly for controlling portion 18 of the holding stem component.

DETAILED DESCRIPTION OF PRESENTLY PREFERRED EMBODIMENTS

Referring to the attached drawings, FIG. 1 shows a general view of the overall structure of the present invention with a partial cross-section of the mirror component. The examination unit 1 is mainly a mirror portion 2 and holding stem portion 3 inside which is located a battery (or a plurality of batteries) 4 which can be replaced through a screw-type end cup 5. A battery-driven type motor 6 is installed at an appropriate position in the holding stem portion 3 further toward the mirror portion 2. The distal end of the motor 6 is connected to a connecting shaft 7. In mirror portion 2 (which is shown in cross-section), there is a T-shaped rotatable disk 9, on which a mirror disk 10 is adhered (adhering means is not shown). The rotatable disk 9 and mirror disk 10 are rotatable inside the circular concave portion 12 which is defined by a surrounding collar 11. The mirror component housing 12a contains the rotatable disk 9 and circular mirror disk 10.

The leg portion of the T-shaped rotatable disk 9 is connected to a shaft 8, which is firmly connected to the connecting shaft 7 by a connecting means 13, such as a gear mechanism or the like.

The longitudinal axis of the connecting shaft 7 in the holding stem portion 3 and the longitudinal axis of the connecting shaft 8 in the mirror portion 2 do not form a straight line, rather they decline at an angle of about 135 degrees. Since this angle is not sharp like a 90 degree angle, a hard rubber tube (not shown in FIG. 1) can be used to connect both shafts 7 and 8. For connecting mechanism 13 for shaft 7 in the holding stem portion 3 and shaft 8 in the mirror portion 2, there can be several ways available. As mentioned above, the shaft axis 7 and shaft axis 8 of the dental mirror are not in a straight line but rather are slightly declined and range from about 120 degrees to 150 degrees. Accordingly, a hard rubber tube can be inserted at the connecting mechanism 13 to both ends of the shafts 7 and 8. As an alternative, a universal joint can be employed as a connecting mechanism 13. Furthermore, a combination of circular cone gears (for example a first gear with 15 degrees as a circular cone angle and a second gear with 45 degrees in order to make a 120-degree bend between the two shafts 7, 8) can be used to accomplish the same movement from rotatable shaft 7 to rotatable shaft 8.

In FIG. 1, there are also ports for lighting means 17, which can be optical fiber connected to installed battery 4 (the connecting means is not shown in FIG. 1). Instead of optical fibers, a single or a plurality of micro-bulbs can be used. An appropriate location for placement of lighting means 17 can be the inner peripheral circle along the circular concave portion 12.

The location of the battery 4 in holding stem portion 3 should be close to the screw-end cup 5. However, the location for motor 6 should be appropriately chosen in such a way that the overall examination unit 1 is evenly balanced so that the operator (in most cases a dental professional) can feel comfortable and not feel any fatigue while he/she is using the examination unit 1.

FIGS. 2A–2C show a manner of applying an adhering agent or tape onto the rear surface of the circular mirror disk 10. In FIG. 1, the outer diameter of mirror 10 is smaller than the inner diameter of the surrounding collar 11 and outer diameter of rotatable disk 9 so that the mirror can be easily attached or detached from the disk 9. Furthermore, for making attachment and detachment of the mirror 10 onto the rotatable disk 9 easier, the adhering agent or double-stick tape can be partially applied to the surface of the rear surface of the mirror 10. For example, as seen in FIG. 2, the adhering material 19 can be applied in a circular form having a diameter smaller than the mirror's diameter as shown in FIG. 2B or in a cross shape. FIG. 2C shows a side view of the mirror 10 and disk 9 with an adhering material therebetween.

FIGS. 3A–3B depict the shape of the surrounding collar 11 defining the circular concave pocket 12 which houses the rotatable disk 10. FIG. 3A shows the top view of the collar 11 and the arrow indicates the direction of rotation of the mirror housing 12. The shape of the periphery of the collar 11 is not a solid doughnut-shape, rather it preferably is formed with a plurality of sub-collars 11a with preferably a sloping portion and a higher level portion. In FIG. 3A, for example, eight (8) equally-divided sub-collars 11a are shown. The highest side of the sub-collar should be on the right side of each sub-collar since the rotating direction of the rotatable disk 10 is in the clockwise direction. When one of the sub-collars 11a in FIG. 3A is viewed from the "x" marked direction and is slightly declined (so that a 3-dimensional view is shown), one sub-collar 11a and two adjacent (partially) sub-collars are shown in FIG. 3B. Again, the arrow indicates the rotating direction of the rotatable disk 9. The principle reason for the sub-collars having an irregular shape, such as a half-cut mountain-shape, is based on the fact that when the rotating disk 9 is rotating, the wind motion should be generated in such a manner that the air turbulence is formed in the surrounding area of the mirror surface 10. As a result, any dust, contaminants, tooth debris or the like, and moisture can be easily spun off the mirror surface 10. Although the shape for sub-collars 11a is shown in FIGS. 3A and 3B as a half-cut mountain-shape, many other shapes can be used so long as air turbulence can be formed to achieve the same purpose as explained above. Moreover, space 11b formed by each sub-collar 11a can provide an open area for contaminants to fly off from the mirror surface. In FIG. 3A, a hole 9a is also shown which provides for passage of the leg portion of the rotatable disk 9.

FIG. 4A shows a connecting means of the rotating shaft 8 of the mirror component 2 to the leg portion of rotatable disk 9 so that the mirror 10 adhered to the disk can rotate. The shaft 8 can be connected to the leg portion of mirror 9 through two 45-degree circular cone gears (or bevel gears) 19, 20. If, for example, the shaft 8 is rotating counterclockwise when viewing the shaft 8 from right to left, the rotatable disk 9 will be rotating clockwise when observing the mirror from the top. FIG. 4B depicts an alternative way to transfer rotating movement to the rotatable disk 9. In this manner, a belt 21 is employed. One end of the belt 21 contacts a leg portion of the disk 9 and the other end thereof is connected to a connecting mechanism 13.

The speed of motor 6 (or accordingly the revolution speed of the rotatable disk 9, and hence as a result mirror disk 10 per se) can be controlled by twisting the controlling portion 18 on the holding stem portion 3, as seen in FIG. 1. FIG. 5 shows a manner of assembly for controlling portion 18. The holding stem portion 3 includes two portions 3a and 3b as shown in FIG. 5A. On the outer surface of portion 3a at its proximal end, there are two small projections 18a and 18b on the circular exterior wall. There are several threads 18c adjacent to these projections. On the other portion 3b, there are the same number of threads 18d as on portion 3a and an arc-formed groove 18e at its distal end. When portions 3a and 3b are connected (in a direction as marked with arrows), these portions 3a, 3b can be twisted via threads 18c, 18d, as shown in FIG. 5B. However, the twisting angle (or distance) is limited within the span confined by the groove 18e since both ends are stopped by the two projections 18a, 18b. The span between these ends also control the upper and lower limits of the rotating speed of the installed motor 6 in FIG. 1. The twisting movement between the two limits confined by projections 18a, 18b is directly connected to the rheostat by which electric voltage can be continuously controlled to drive the motor 6.

With regard to rotating speed, although the battery-driven motor 6 can rotate up to 360 r.p.m., it was found that the appropriate rotation speed in use ranges from between 120 and 240 r.p.m. in order to spin off any debris, dust, contaminants, and moisture from the mirror surface effectively and efficiently. If the rotating speed is less than 120 r.p.m., sticky and heavy contaminants may not be removed completely. On the other hand, although the mirror can be rotated higher than 360 r.p.m., it was found that about 240 r.p.m. is the highest rotating speed necessary in order to maintain a particle-free and moisture-free clean mirror surface. When spin tests were conducted, the mirror adhered to the rotating disk was an ordinary double-stick type. It was found that the mirror remained firmly adhered to the rotating disk even after continuous rotating at 360 r.p.m. for 1 hour while continuously applying water droplets onto the mirror surface.

Applying water onto the dental mirror can help further to keep the mirror clean. Normally, when a dentist is using a burr drill, the tooth structure under preparation is kept cool by spraying water continuously. Therefore, inclusion of a water spraying device in the present dental mirror is advantageous.

While the invention has been described with reference to the structure and function disclosed herein, the invention is not confined to the details as set forth. The application is intended to cover modifications and changes as may come within the scope of the claims.

What is claimed is:

1. A mirror for examining a confined area comprising a mirror component and a holding stem component; said mirror component and said holding stem component being connected at approximately a 120 to 150 degree angle to form a unified structure; wherein the mirror component includes a circular concave housing with one central opening through which a leg portion of a rotatable disk is inserted, a circular-shaped mirror with a diameter less than a diameter of the rotatable disk and which is adhered to a top surface of said rotatable disk, said rotatable disk with adhered mirror disk being adapted to rotate inside the circular concave housing of the mirror component, said circular concave housing including a collar portion having a plurality of irregular-shaped sub-collars, said sub-collars providing open spaces through which solid and liquid particles can escape from the mirror surface, at least one lighting device along an inner peripheral circle of said circular concave housing adapted to illuminate a visible surface of the mirror; a connecting means connected to a motor adapted to transfer rotating movement from the motor to the mirror, said connecting means including a shaft connected to the motor which is present in the holding stem component wherein the holding stem component further includes a power supply operatively connected to the motor and said at least one lighting device, a component electrically connected to a mechanism which controls the rotating speed of the motor, and an on/off switch for controlling power to said motor.

2. The mirror of claim 1, wherein the connecting means can include either a rubber tube, a universal joint, or bevel gears.

3. The mirror of claim 1, wherein the power supply is at least one battery.

4. The mirror of claim 3, wherein the battery is either disposable or rechargeable.

5. The mirror of claim 1, wherein the rotatable disk is adapted to rotate at a speed in a range from 120 r.p.m. to 360 r.p.m.

6. The mirror of claim 1, wherein the leg portion of the rotating disk is operatively connected to the motor by means of a shaft with bevel gears or a belt.

7. The mirror of claim 1, wherein between eight to twenty-four sub-collars are present.

8. The mirror of claim 1, wherein each irregular-shaped sub-collar is shaped to include a higher portion and a lower portion, said lower portion providing said open spaces for escape of the solid or liquid particles.

* * * * *